(12) United States Patent
Montaser et al.

(10) Patent No.: US 7,145,137 B2
(45) Date of Patent: Dec. 5, 2006

(54) DEMOUNTABLE DIRECT INJECTION HIGH EFFICIENCY NEBULIZER FOR INDUCTIVELY COUPLED PLASMA MASS SPECTROMETRY

(75) Inventors: Akbar Montaser, Potomac, MD (US); Craig S. Westphal, Landenberg, PA (US); Kaveh Kahen, Montgomery Village, MD (US); William F. Rutkowski, Arlington, VA (US); Billy W. Acon, Arlington, VA (US)

(73) Assignee: The George Washington University, Washington, DC (US)

( * ) Notice: Subject to any disclaimer, the term of this patent is extended or adjusted under 35 U.S.C. 154(b) by 0 days.

(21) Appl. No.: 11/019,098

(22) Filed: Dec. 22, 2004

(65) Prior Publication Data
US 2005/0230617 A1    Oct. 20, 2005

Related U.S. Application Data

(60) Provisional application No. 60/531,685, filed on Dec. 23, 2003.

(51) Int. Cl.
  *H01J 49/00*    (2006.01)
(52) U.S. Cl. ...................... 250/288; 250/289
(58) Field of Classification Search .............. None
  See application file for complete search history.

(56) References Cited

U.S. PATENT DOCUMENTS

| | | | | |
|---|---|---|---|---|
| 3,550,858 | A | * | 12/1970 | Larrabee et al. ............ 239/338 |
| 3,552,657 | A | * | 1/1971 | Chisholm et al. ........... 239/424 |
| 4,125,225 | A | * | 11/1978 | Venghiattis ................. 239/338 |
| 4,517,495 | A | | 5/1985 | Piepmeier |
| 4,990,740 | A | | 2/1991 | Meyer |
| 5,066,125 | A | | 11/1991 | Rogers |
| 5,884,846 | A | * | 3/1999 | Tan ............................. 239/338 |
| 6,126,086 | A | * | 10/2000 | Browner et al. ......... 239/102.1 |
| 6,166,379 | A | * | 12/2000 | Montaser et al. ........... 250/288 |
| 6,729,334 | B1 | * | 5/2004 | Baran .................... 128/207.14 |

OTHER PUBLICATIONS

A. Montaser; "Inductively Coupled Plasma Mass Spectrometry"; Wiley-VCH, New York, 1998.
J.A. McLean, H. Zhang, and A. Montaser; "A Direct Injection High Efficiency Nebulizer for Inductively Coupled Plasma Mass Spectrometry"; Anal. Chem 70; 1012-1020; 1998.
L. Bendahl, B. Gammelgaard, O Jons, O. Farver, and S.H. Hansen; Interfacing Capillary Electrophoresis with Inductively Coupled Plasma Mass Spectrometry by Direct Injection Nebulization for Selenium Speciation: J. Anal. At. Spectromm. 16, 38-42 (2001).
B. Gammelgaard, L. Bendahl, U.Sidenius, and O. Jons; "Selenium Speciation in Urine by Ion-Paring Chromatography with Perfluorinated Carboxylic Acids and ICP-MS Detection"; J. Anal. At. Spectrom. 17,570-575 (2002).
J. Wang and E.H. Hansen; "Interfacing Sequential Injection On-Line Preconcentration Using a Renewal Micro-Column Incorporated in a 'Lab-on-Valve' System with Direct Injection Nebulization Inductively Coupled Plasma Mass Spectrometry"; J. Anal. At. Spectrom. 16, 1349-1355 (2001).

* cited by examiner

*Primary Examiner*—Nikita Wells
*Assistant Examiner*—Anthony Quash
(74) *Attorney, Agent, or Firm*—Roylance, Abrams, Berdo & Goodman, LLP

(57) ABSTRACT

A nebulizer adapted for adjusting a position of a capillary tube contained within the nebulizer is provided. The nebulizer includes an elongated tubular shell having a gas input port and a gas output port, a capillary adjustment adapter for displacing the capillary tube in a lateral direction via a rotational force, and a connector for connecting the elongated tubular shell, the capillary adjustment adapter and the capillary tube.

19 Claims, 13 Drawing Sheets

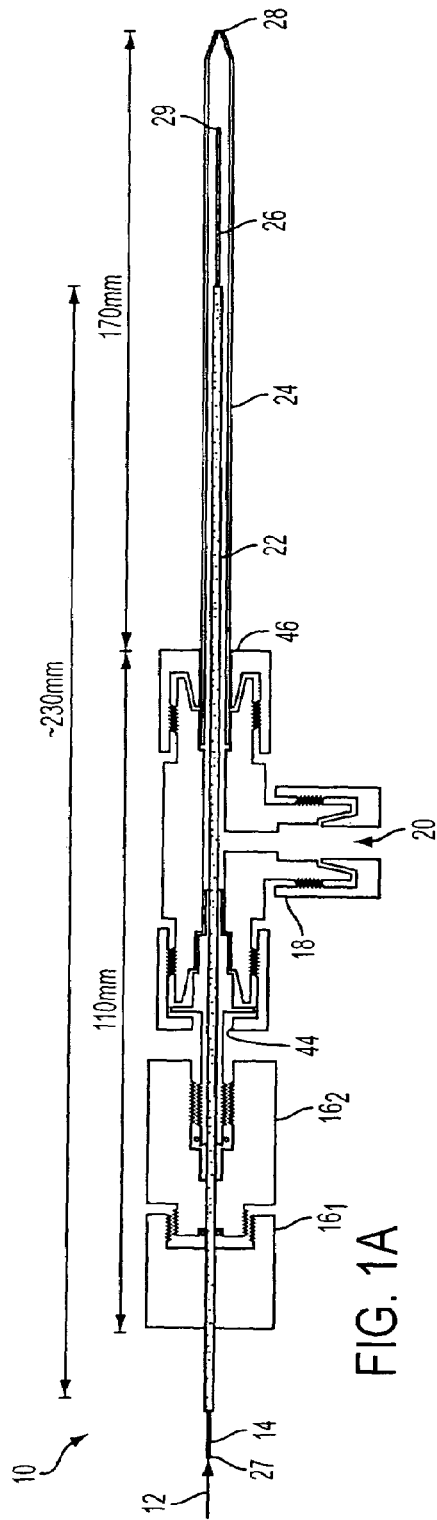
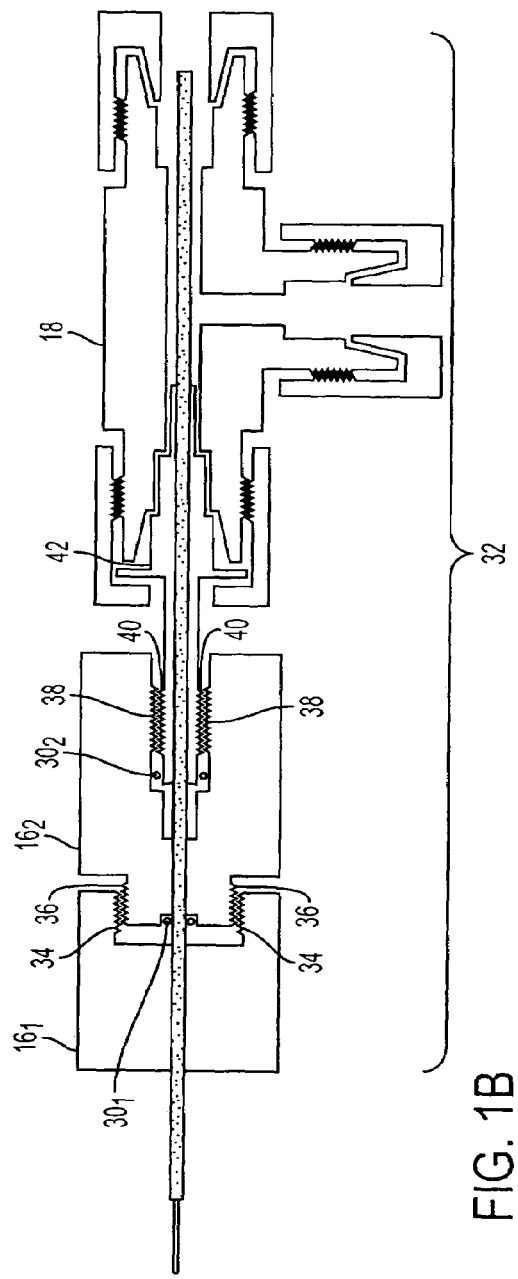
FIG. 1A
FIG. 1B

DEMOUNTABLE DIRECT INJECTION HIGH EFFICIENCY NEBULIZER FOR INDUCTIVELY COUPLED PLASMA MASS SPECTROMETRY

PRIORITY

The present application claims priority from U.S. Provisional Patent Application Ser. No. 60/531,685, entitled "Demountable Direct Injection High Efficiency Nebulizer For Inductively Coupled Plasma Mass Spectrometry", filed on Dec. 23, 2003, the entire content of which is incorporated herein by reference.

CROSS REFERENCE TO RELATED PATENT

Related subject matter is disclosed in U.S. Pat. No. 6,166,379, entitled "Direct Injection High Efficiency Nebulizer For Analytical Spectrometry", issued on Dec. 26, 2000 to Akbar Montaser et al, the entire content of which is incorporated herein by reference. Related subject matter is also disclose in U.S. Nonprovisional Patent Application No. 11/018,919 filed concurrently with the present application.

This application was made with United States Government support under Grant No. DE-FG02-93ER14320 awarded by the U.S. Department of Energy. The U.S. Government has certain rights in the invention.

BACKGROUND OF THE INVENTION

1. Field of the Invention

This application relates generally to nebulizers for use in analytical spectrometry such as inductively coupled mass spectrometry, and more specifically to direct injection nebulizers.

2. Description of the Related Art

Inductively coupled plasma atomic emission spectrometry (ICPAES) and ICP mass spectrometry (ICPMS) are practical techniques for trace and ultratrace elemental analysis. While many advances have been made in instrumentation, the introduction of a sample to the plasma represents the most problematic area, with liquid sample introduction being the most common. Many devices have been developed for aerosol generation and transport, each having its own benefits and limitations.

The pneumatic nebulizer-spray chamber arrangement is currently the primary sample introduction method for ICP spectrometry, mainly due to its simplicity and low cost. This arrangement presents, however, several drawbacks, namely low analyte transport efficiency (1–20%) and high sample consumption (1–2 mL/min), memory effects, spray chamber-induced interferences such as transient acid effects, and post-column broadening when coupled with chromatographic techniques for speciation analysis. These effects may be reduced through the use of micronebulizers and reduced-volume spray chambers integrated with⁻ or without⁻ the ICP torch. A simple, low-consumption, highly efficient nebulizer is often required in chromatographic applications and also for the direct analysis of semiconductor, biological, toxic, or forensic materials. In these and other cases, the sample is expensive, hazardous, or limited.

Two popular micronebulizers have been explored that eliminate the need for the spray chamber by directly introducing 100% of the sample into the plasma: the direct injection nebulizer (DIN) and the direct injection high efficiency nebulizer (DIHEN). Both devices offer fast response times, reduced memory effects, no transient acid effects, no solution waste and low sample consumption rates (1–100 µL/min) while exhibiting similar or improved detection limits, sensitivity and precision compared to conventional nebulizer-spray chamber arrangements. Although the DIN has an adjustable and exchangeable solution capillary, its versatility is limited due to its relatively complex setup, high costs, and requirement of a high-pressure pump for sample delivery. The DIHEN, however, is a simple concentric nebulizer that is less expensive compared to the DIN and does not require an additional high-pressure pump.

One weakness of the micronebulizers (including the DIN and DIHEN) in addition to their high cost is their greater susceptibility to nebulizer clogging compared to other types of nebulizers due to the smaller dimensions for the solution capillary and gas annulus areas. This limitation may destroy the nebulizer. In order to overcome the problem of clogging a large bore-DIHEN (LB-DIHEN) is used. Although nebulizer clogging is reduced for nebulization of slurries and solutions having a large amount of total dissolved solids, the performance of the LB-DIHEN is slightly worse than those of the DIHEN. Additionally, the close proximity of the nebulizer tip to the plasma increases the likelihood of accidental and gradual damage to direct injection nebulizers.

Accordingly, there is a need for a simple, low cost device that allows easy replacement of a solution capillary due to, for example, clogging or melting. In addition, the device should also allow for precise alignment of the capillary tip with respect to the nebulizer tip not only to improve nebulization, but also to increase the distance between the nebulizer tip and the plasma base, thereby protecting the nebulizer against melting

SUMMARY OF THE INVENTION

A low cost, demountable direct injection high efficiency nebulizer (d-DIHEN) in accordance with embodiments of the present invention provides an adjustable solution capillary, allowing improvement of the operational characteristics of the micronebulizers, aerosol properties, and analytical figures of merit in inductively coupled plasma (ICP) spectrometries.

According to an aspect of the present invention, a nebulizer with an adjustable capillary position with respect to the body of the nebulizer is provided. The nebulizer includes an elongated tubular shell having a gas input port and a gas output port, a capillary adjustment adapter for displacing the capillary tube in a lateral direction via a rotational force, and a connector for connecting the elongated tubular shell, the capillary adjustment adapter and the capillary tube.

According to another aspect of the present invention, a modular nebulizer is provided. The modular nebulizer comprises an elongated tube having an open first end and a tapered second end leading to a nozzle, and a connector for connecting the elongated tube to a sample and to a gas.

BRIEF DESCRIPTION OF THE DRAWINGS

These and other objects, advantages and novel features of the invention will be more readily appreciated from the following detailed description when read in conjunction with the accompanying drawings, in which:

FIGS. 1A through 1F are diagrams of a demountable direct injection high efficiency nebulizer with a tunable solution capillary in accordance with embodiments of the present invention;

Figure 3A:
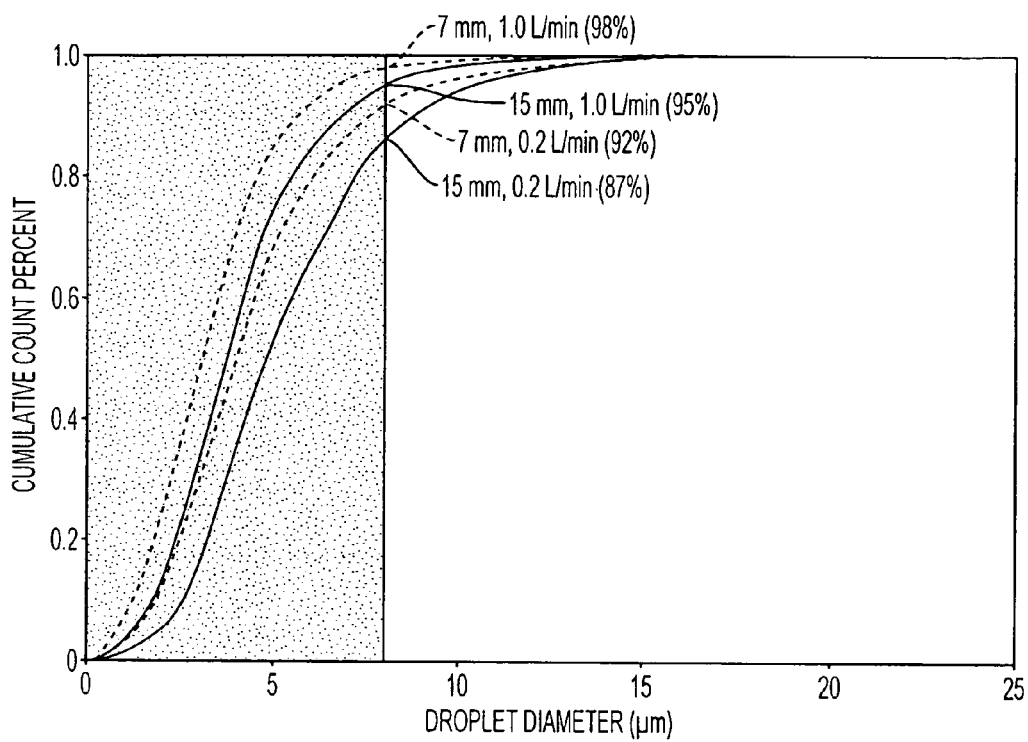
Figure 3B:
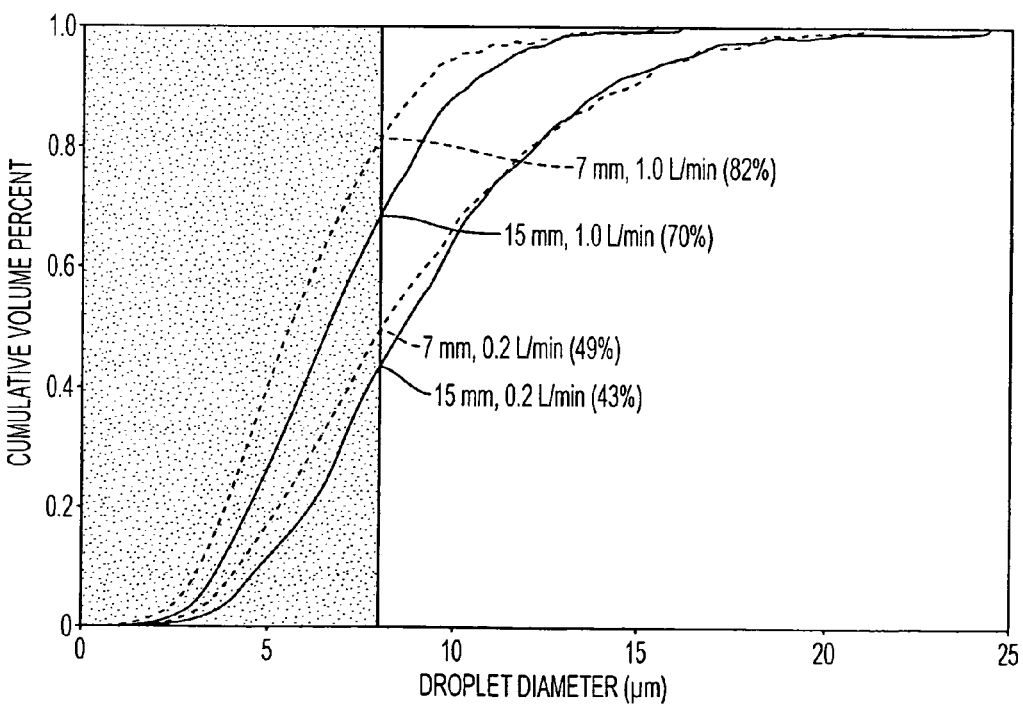
Figure 4A:
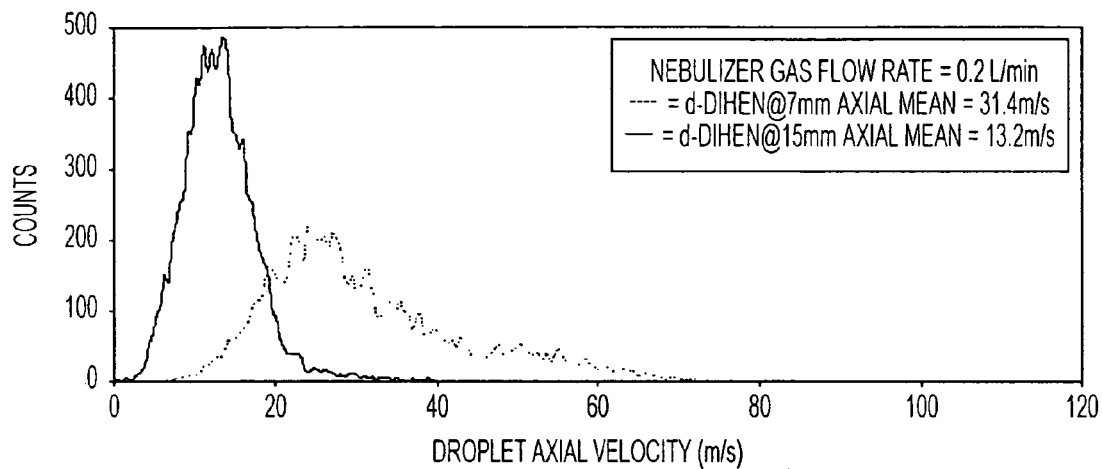
Figure 4B:
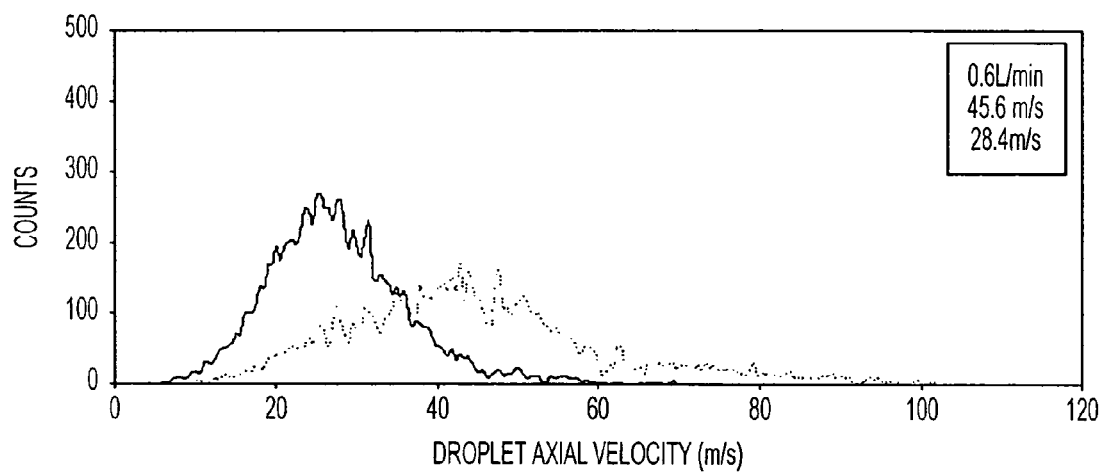
Figure 4C:
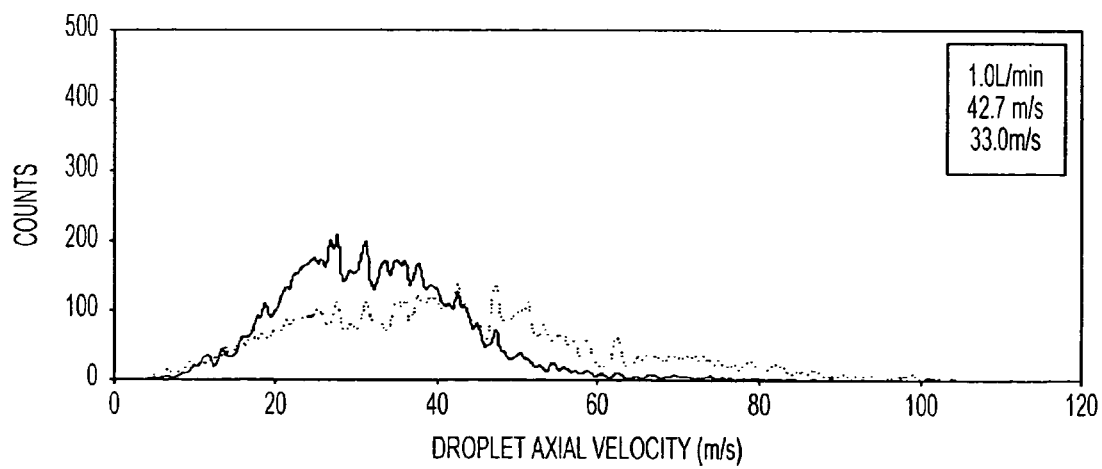
Figure 4D:
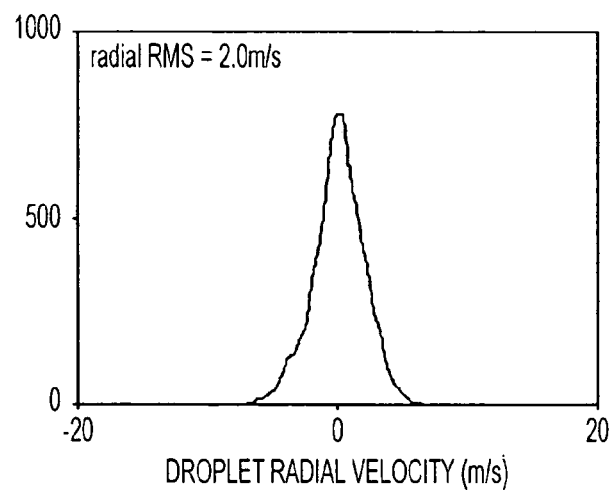
Figure 4E:
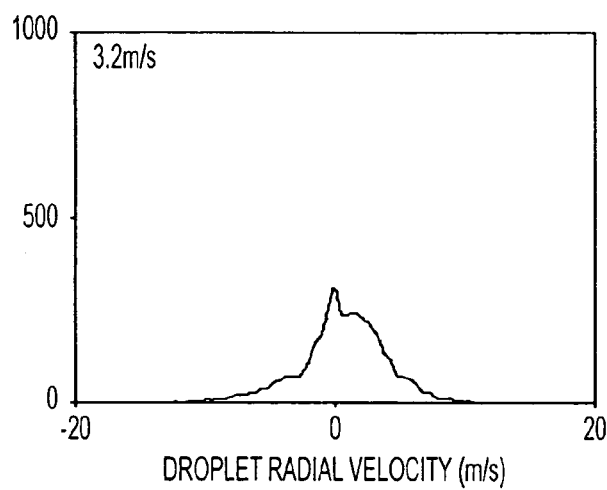
Figure 4F:
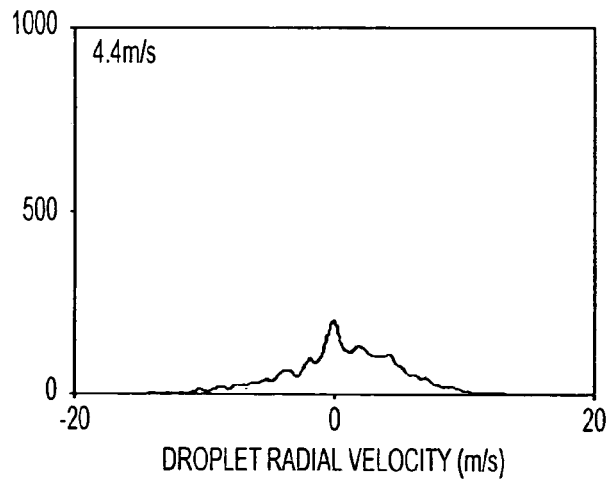
Figure 5A:
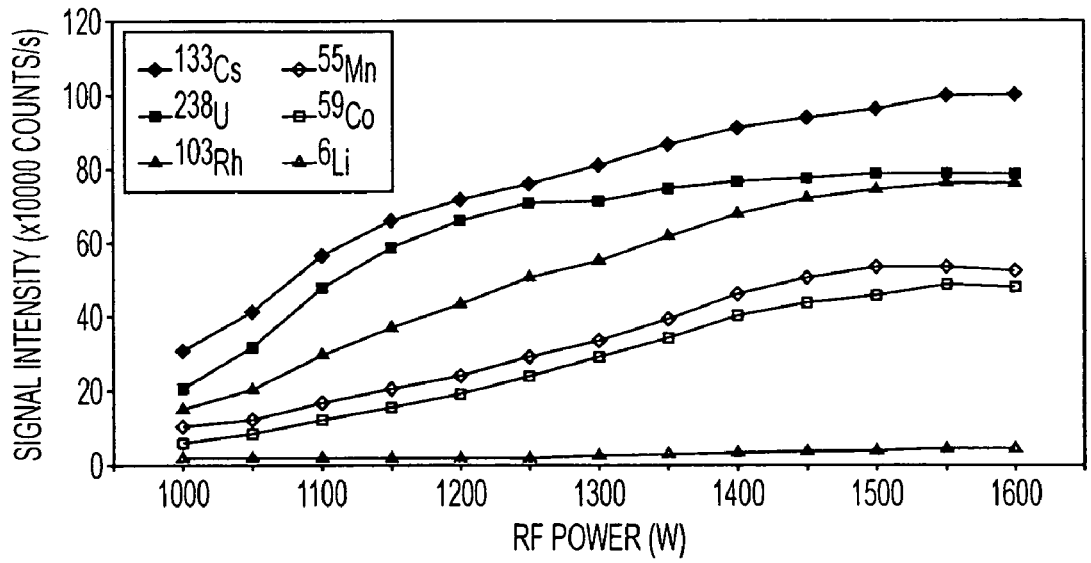
Figure 5B:
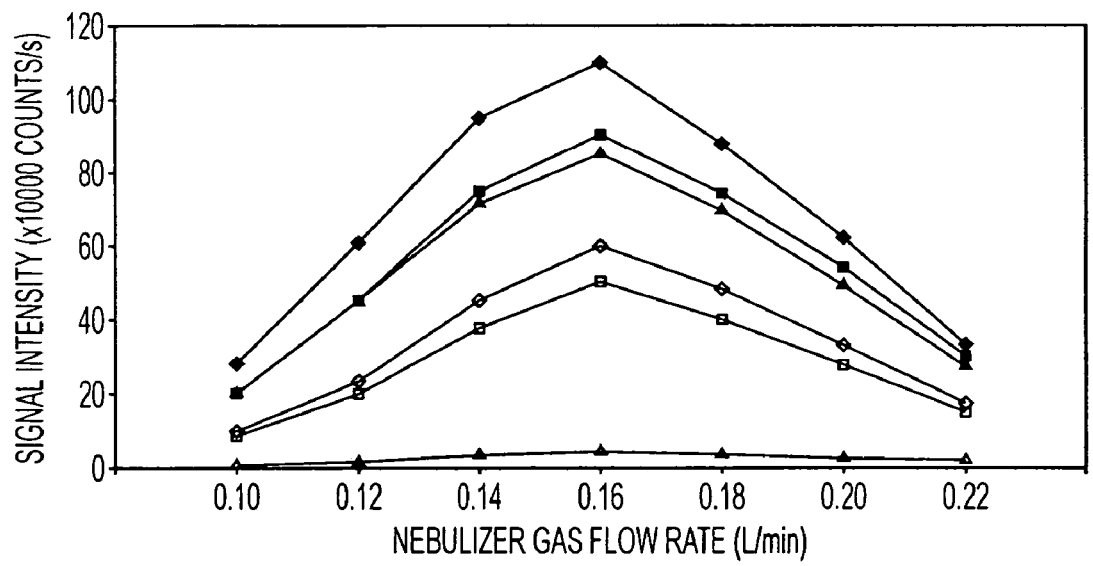
Figure 5C:
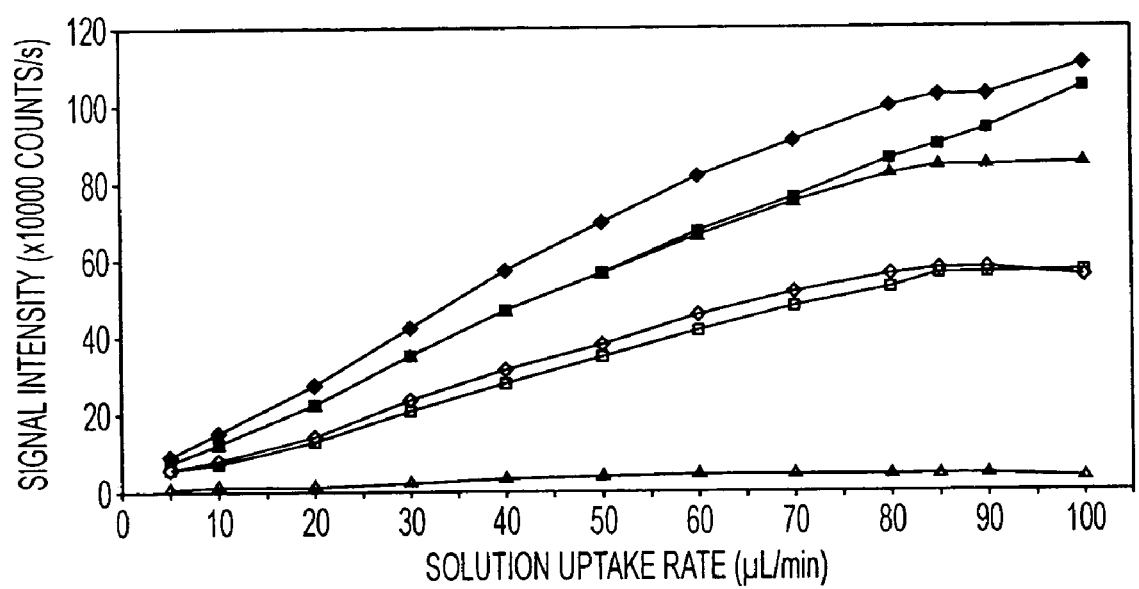

normalized volume percent as a function of nebulizer gas flow rate for the d-DIHEN at 7 mm (dashed line) and 15 mm (solid line) from the tip of the nebulizer in accordance with an embodiment of the present invention;

FIGS. 3A and 3B are graphs illustrating cumulative count and mass (or volume) percent as a function of droplet diameter in accordance with an embodiment of the present invention;

FIGS. 4A through 4F are graphs illustrating a variation of axial and radial droplet velocity distributions as a function of nebulizer gas flow rate for the d-DIHEN at 7 mm (dashed line) and 15 mm (solid line) from the tip of the nebulizer in accordance with an embodiment of the present invention; and FIGS. 5A through 5C are graphs illustrating signal intensity as a function of RF power (A), nebulizer gas flow rate (B), and solution uptake rate (C) in accordance with an embodiment of the present invention.

DETAILED DESCRIPTION OF THE PREFERRED EMBODIMENTS

A schematic diagram of an embodiment of a demountable direct injection high efficiency nebulizer 10 (d-DIHEN) is shown in FIGS. 1A through 1E. The d-DIHEN 10 comprises a capillary adjustment adapter 16 comprising a compressing member $16_1$ and a lateral movement member $16_2$, a connector 18, and an elongated tubular shell 24 preferably comprising borosilicate glass. The d-DIHEN 10 includes a capillary 26, which is preferably a solution capillary having an input sample port 27 for accepting a sample 12, and an output sample port 29. The capillary tube 26 is preferably a polyimide coated fused silica capillary having dimensions of 100 μm i.d.×165 μm outer diameter (o.d). A supporting tube 22, preferably a PEEK capillary tubing preferably having the dimensions 175 μm i.d.×1/16-in.-o.d., is used to protect the capillary 26 from damage and from wobbling when the capillary 26 is adjusted by the capillary adjustment adapter 16. A sleeve 14 is preferably disposed between the capillary 26 and the supporting tube 22.

The connector 18 preferably comprises Teflon and preferably is a T connector, but it should be appreciated by those skilled in the art that the connector 18 may comprise other materials such as glass for example, Macor, metal and high temperature resistant plastics without departing from the scope of the present invention. The connector 18 connects the capillary adjustment adapter 16 via an input port 44 and connects the elongated tubular shell 24 via an output port 46. It should be appreciated by those skilled in the art that the connector 18 and elongated tubular shell 24 comprise a modular design for a nebulizer.

Figure 1C:
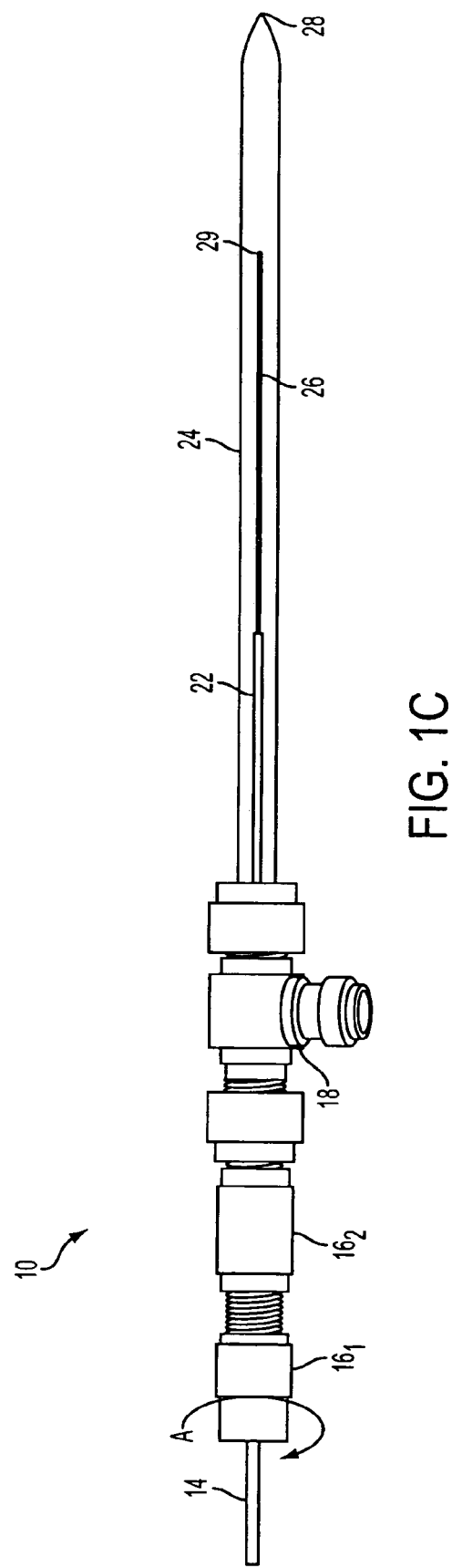

A detailed description of the housing 32 and interconnected parts therein of the d-DIHEN 10 with reference to FIGS. 1B and 1C. The compressing member $16_1$ includes a female threaded section 34 interacting with a male threaded section of the lateral moving member $16_2$. The lateral moving member $16_2$ also includes a female threaded section 38 that interacts with a male threaded section 40 of an inner connector supporting member 42 of the connector 18. Disposed on a smooth surface proximate the female threaded section 38 of the lateral moving member $16_2$ and a smooth inner circumference of the male threaded section 36 of the lateral moving member $16_2$ and the male threaded section 40 of an inner connector supporting member 42 of the connector 18 are O-rings 30.

In an embodiment of the present invention, as the compressing member $16_1$ is rotated in the direction of "A" the compressing member $16_1$ moves forward and exerts pressure on O-ring $30_1$ via engagement of the female threaded section 34 with the male threaded section 36. That is rotation of the compressing member $16_1$ selectively exerts pressure on the O-ring $30_1$. Increased rotation of the compressing member $16_1$ exerts increased pressure on the O-ring $30_1$. The pressure on O-ring $30_1$ serves to provide the lateral moving member $16_2$ with a firm grip on the supporting tube 22, the sleeve 14 and/or the capillary tube 26 in order to move the capillary tube 26 in a lateral direction.

O-ring $30_2$ is disposed between a smooth surface of female threaded section 38 and a smooth surface of male threaded section 40. When lateral moving member $16_2$ is rotated in the direction of "D", O-ring $30_2$ serves to reduce vibrations and sudden movements due to the rotational engagement of the female threaded section 38 and male threaded section 40.

It should be appreciated by those skilled in the art that although O-rings are used as examples, any type of compressive substance can be substituted and still fall within the scope of the present invention. In addition, in an embodiment of the present invention, capillary adjustment adapter 16 may comprise a single device rather than comprise two units.

Figure 1D:
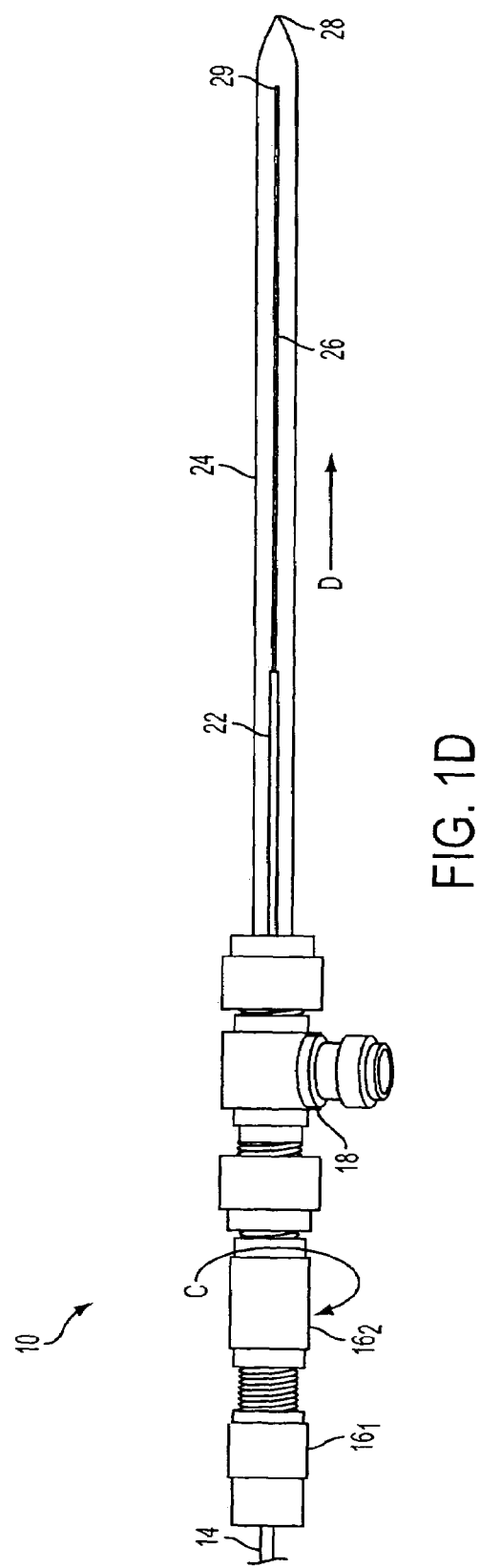
Figure 1E:
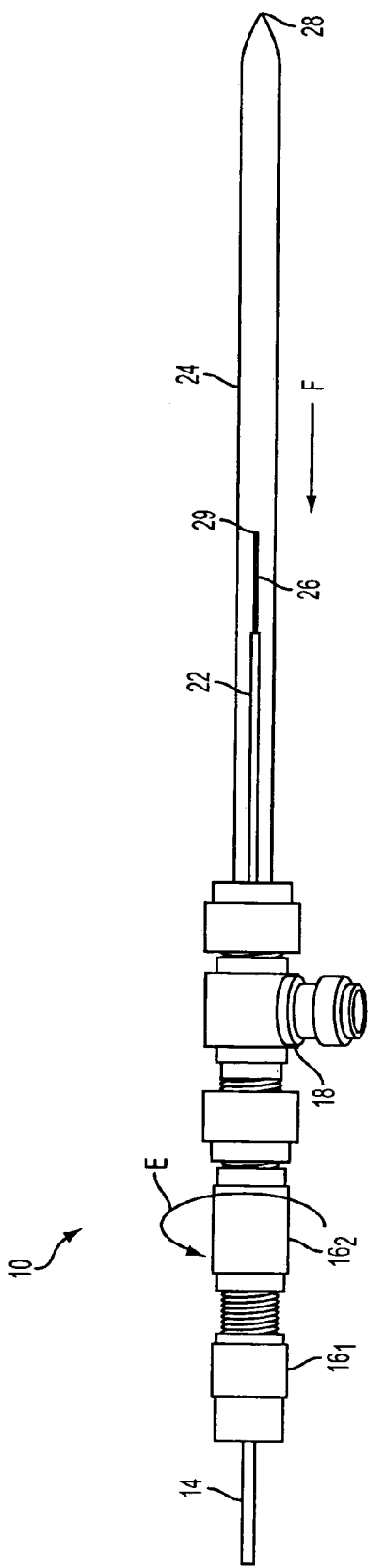

A description of an embodiment of the invention will now be described with reference to FIGS. 1D and 1E. When lateral moving member $16_2$ is rotated in the direction of "C", the output port 29 of the capillary tube 26 is displaced in the direction of "D" as shown in FIG. 1D. That is, the output port 29 of the capillary tube 26 approaches the nozzle 28 of the elongated tubular shell 24. When lateral moving member $16_2$ is rotated in the direction of "E", the output port 29 of the capillary tube 26 is displaced in the direction of "F" as shown in FIG. 1D. That is, the output port 29 of the capillary tube 26 moves away from the nozzle 28 of the elongated tubular shell 24. It should be appreciated by those skilled in the art that the present invention is not limited to the direction of rotation and the direction of lateral movements shown.

Figure 1F:
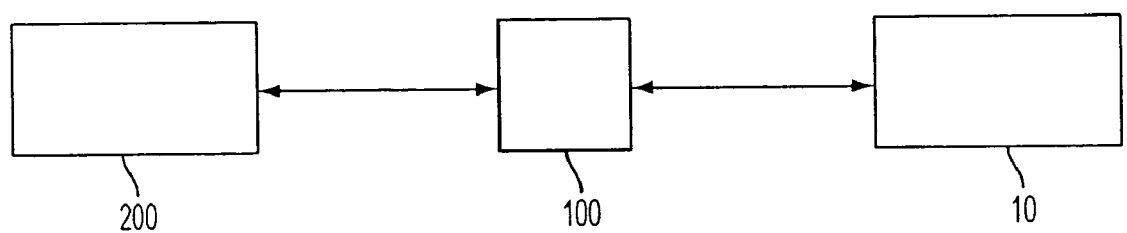
Figure 2A:
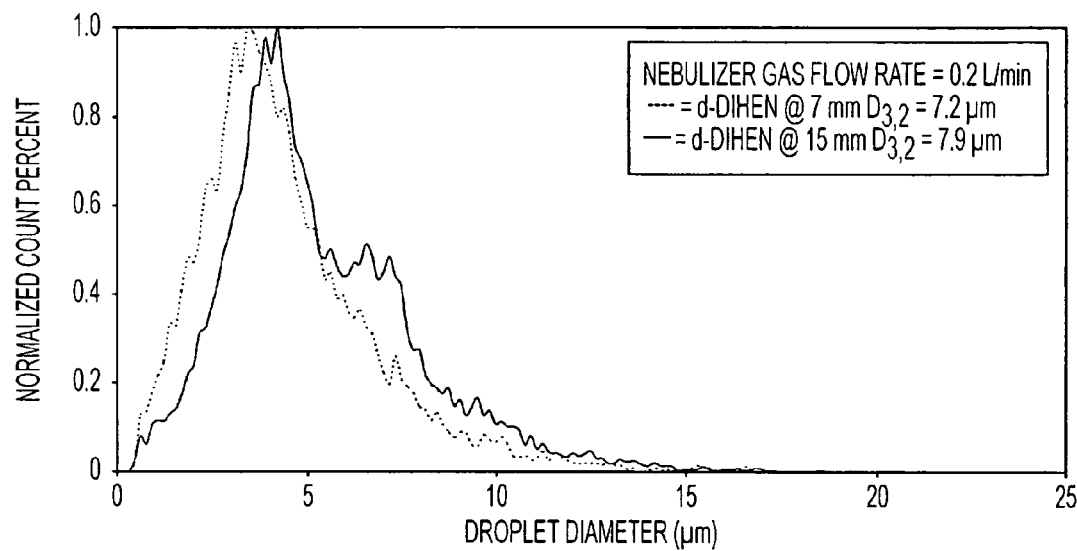
FIGS. 2A through 2F are graphs illustrating droplet size distributions in (A) normalized count percent and in (B)
Figure 2B:
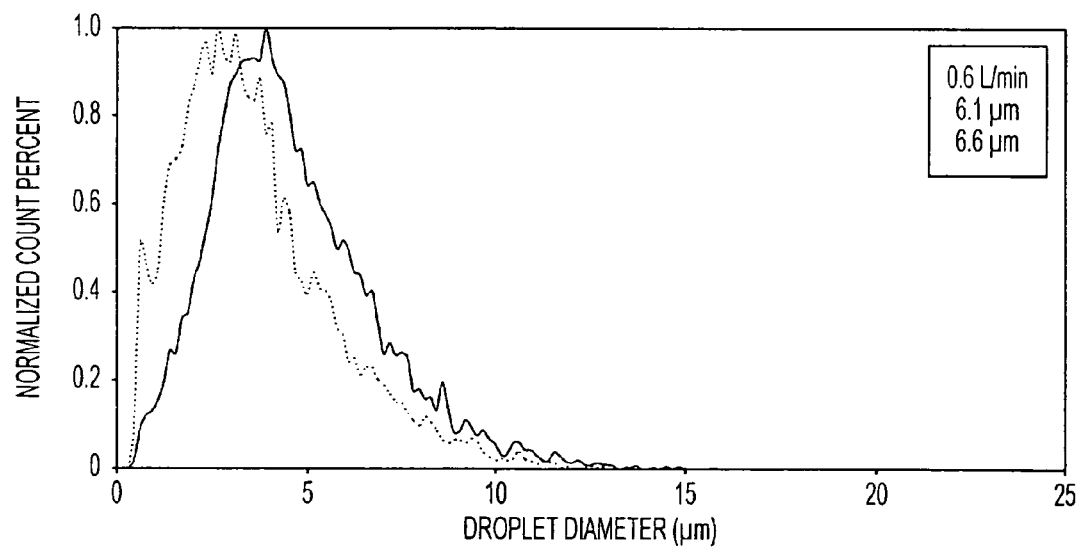
Figure 2C:
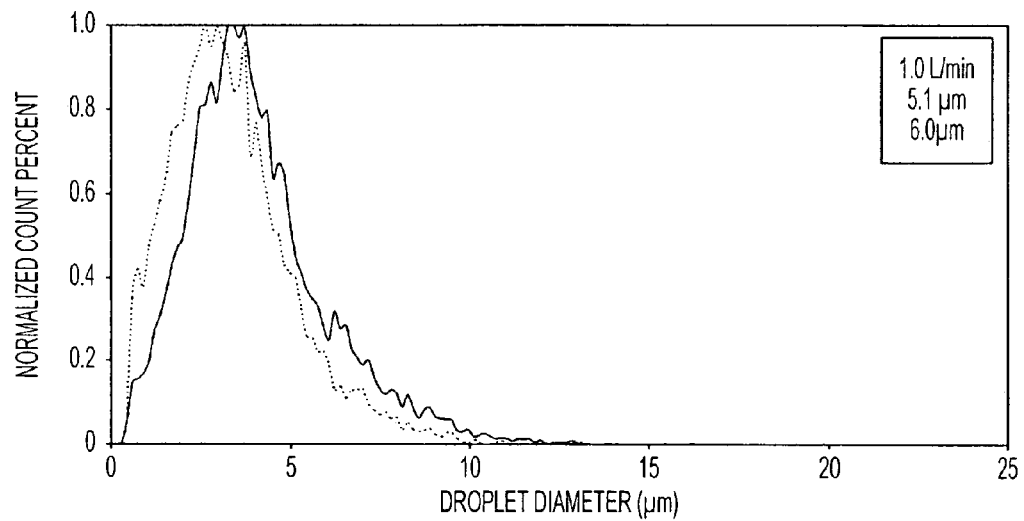
Figure 2D:
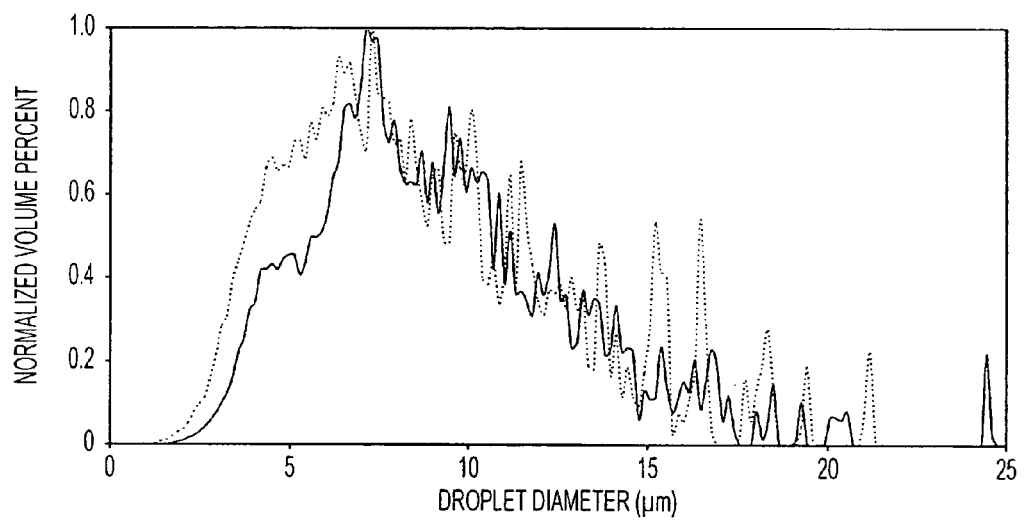
Figure 2E:
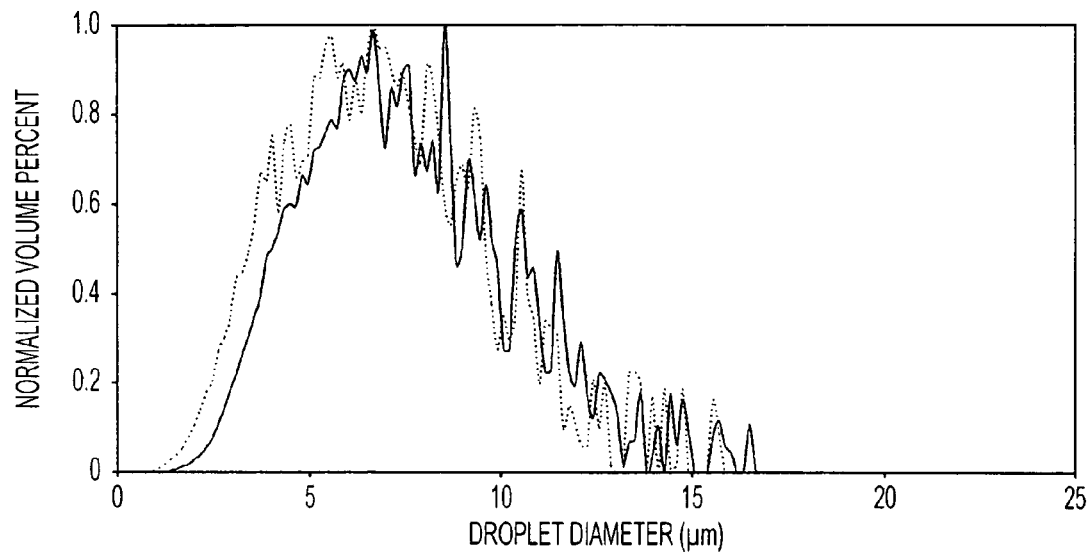
Figure 2F:
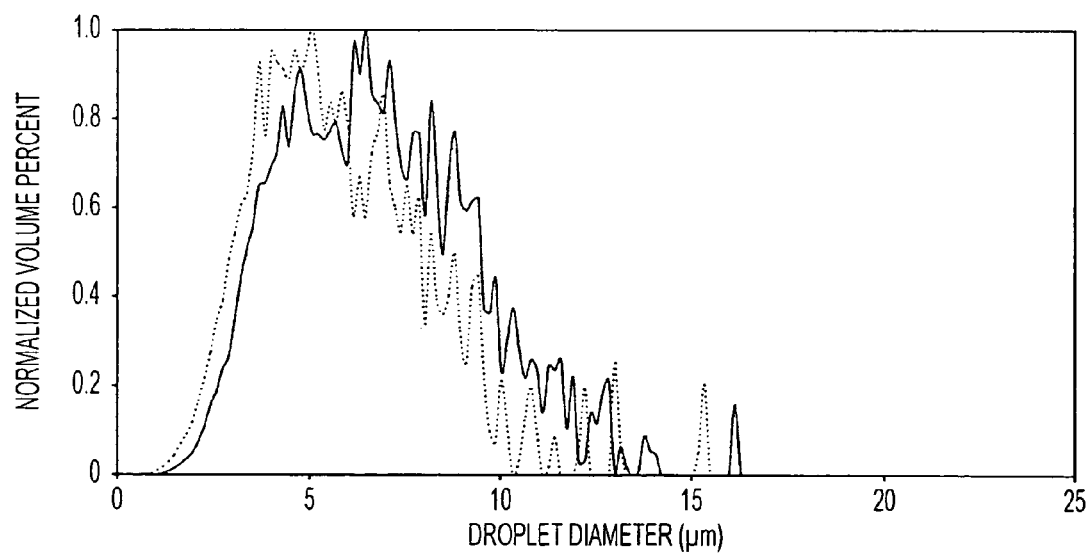

An embodiment of the present invention will now be described with reference to FIG. 1F. FIG. 1F discloses a computer 200, connected to a controller 100, which is in turn connected to the d-DIHEN 10. In an embodiment of the invention, a user can input the exact distance the output port 29 of the capillary tube 26 needs to be from the nozzle 28 of the elongated tubular shell 24. The controller 100 then operates a motor which is connected to the capillary adjustment adapter 16 in order to position the output port 29 of the capillary tube 26. The user can detect the displacement of the capillary tube 26 via a monitor on the computer 200.

In another embodiment of the present invention, the user can use a keypad or toggle device on the computer 200 to displace the capillary tube 26 via the controller 100. The capillary adjustment adapter 16 can be calibrated to allow the controller 100 to provide feedback concerning rotational displacement of the capillary adjustment adapter 16, which can then be converted to lateral displacement of the capillary tube 26. It should be appreciated by those skilled in the art that the controller 100 and computer 200 can be contained in a single unit without departing from the scope of the present invention.

Table 1 contains key dimensions of the exemplary d-DIHEN 10 with respect to conventional nebulizers. The design of the d-DIHEN 10 is based on the DIHEN which is disclosed in J. S. Becker, H.-J. Dietze, J. A. McLean, and A. Montaser, Ultratrace and Isotopic Analysis of Long-Lived Radionuclide by Inductively Coupled Plasma Quadrupole Mass Spectrometry Using a Direct Injection High Efficiency Nebulizer, *Anal. Chem.* 71, 3077–3084 (1999) and M. G. Minnich and A. Montaser, Direct Injection High Efficiency Nebulization in Inductively Coupled Plasma Mass Spectrometry Under Cool and Normal Plasma Conditions, *Appl. Spectrosc.* 54, 1261–1269 (2000) and the homemade DIHEN, which is disclosed in L. Bendahl, B. Gammelgaard, O. Jøns, O. Farver, and S. H. Hansen, Interfacing Capillary Electrophoresis with Inductively Coupled Plasma Mass Spectrometry by Direct Injection Nebulization for Selenium Speciation, *J. Anal. At. Spectrom.* 16, 38–42 (2001), B. Gammelgaard, L. Bendahl, U. Sidenius, and O. Jøns, Selenium Speciation in Urine by Ion-Pairing Chromatography with Perfluorinated Carboxylic Acids and ICP-MS Detection, *J. Anal. At. Spectrom.* 17, 570–575 (2002), J. Wang and E. H. Hansen, Interfacing Sequential Injection On-Line Preconcentration Using a Renewable Micro-Column Incorporated in a 'Lab-on-Valve' System with Direct Injection Nebulization Inductively Coupled Plasma Mass Spectrometry, *J. Anal. At. Spectrom.* 16, 1349–1355 (2001). All of which are incorporated herein by reference. However, the cited references lack the modular design and the capillary adjustment adapter 16 feature of the embodiment of the present invention. As previously discussed, the capillary adjustment adapter 16 allows for the precise positioning and tuning of the solution capillary 26 position with respect to the nebulizer tip 28.

The capillary adjustment adapter 16 is designed and constructed in-house to allow for precise positioning of the solution capillary 26. One complete revolution of the capillary adjustment adapter 16 preferably provides approximately 0.3 mm lateral movement of the capillary tube 26. The nebulizer gas is directed through the elongated tubular shell 24 the bottom opening or gas input port 20 of the connector 18 and is controlled by an external mass flow controller not shown preferably a model 8200, manufactured by Matheson Gas Products. To maintain a nebulizer gas flow rate of 0.2 L/min, a backpressure of 20 psig is required on the d-DIHEN 10. The solution capillary 26 comprises a polyimide-coated fused silica capillary that extends through the entire length of the d-DIHEN 10. To enhance solution-gas interactions and improve nebulization, the final segment (approximately 20 mm) of polyimide coating is removed by burning it using an open flame, reducing the capillary 26 wall thickness to approximately 20 µm. The solution capillary is supported by a PEEK tube 22, which extends up to 70 mm below the nebulizer tip 28. A microtight sleeve 14 preferably having dimensions of 178 µm i.d.×635 µm o.d. and a fingertight nut (not shown) preferably having dimensions of 0.025-in.-i.d., 6·32, connect the solution capillary 26 to the solution delivery pump (not shown). The end of the solution capillary 26 is cut using a fused silica capillary cutter to ensure a smooth, flush end. Ceramic cutters are not recommended as they often result in an imprecisely cut tip, which in turn produce an asymmetric spray and poor analytical figures of merit.

Test solution is delivered to the d-DIHEN 10 using either a syringe pump (not shown) or a four-channel peristaltic pump (not shown). In the latter case, a narrow-bore Tygon tubing preferably having dimensions of 0.015-in.-i.d. is utilized to reduce peristaltic-related noise. The nebulizer dead volume is 11 µL measured experimentally. In contrast to the DIHEN or LB-DIHEN, no special connections are necessary to minimize the dead volume of the d-DIHEN 10 because the solution capillary 26 extends the entire length of the nebulizer. Further, no special high-pressure pump is required to deliver solution to the d-DIHEN 10 as long as the fused silica capillary 26 has an i.d. of at least 100 µm. For capillaries with smaller internal diameters, leaking occurs at the junction of the peristaltic pump and PEEK tubing due to the increased backpressure.

For comparison purposes, a DIHEN (model DIHEN-120-AA, Meinhard Glass Products, Analytical Reference Materials International Corp.) is also used for comparison. The DIHEN and the d-DIHEN 10 are interfaced with the ICPMS. The nebulizer gas is externally controlled using a preferably a model 8200 and optimized at 0.18 L/min for maximum ion intensity of $^{103}Rh^+$. Solution is delivered using a syringe pump preferably a model 100, KD Scientific.

Analytical characteristics of the d-DIHEN 10 are investigated using an Elan 6000 ICPMS system manufactured by Perkin-Elmer/Sciex Corp., Norwalk, Conn. under the operating conditions listed in Table 2. All analytical data are obtained under standard laboratory conditions (e.g., not in a clean-room environment). The system is optimized daily for maximum ion intensity of $^{103}Rh^+$. All data are collected in the peak-hopping mode with a dwell time of 20 ms and total integration time of 1 s/mass unless otherwise noted. The lens voltage is auto-optimized for each m/z.

A two-dimensional phase Doppler particle analyzer using a 2D-PDPA, Aerometrics/TSI Inc., St. Paul, Minn. is used for aerosol diagnostic studies of the droplet-size and velocity distributions. Details of this 2D-PDPA system are known to those skilled in the art. Four photomultiplier tubes are operated at −501 V. The receiver optics are held at a forward scattering angle of 30° with respect to the transmitter by placing both the receiver and transmitter on separate 15° inclined planes. With this arrangement, the d-DIHEN 10 aerosol is probed horizontally as it is used in ICPMS. The probe volume width is approximately 120 μm using a 250-mm focal length transmitting lens and a beam separation of 41 mm. Comparison of the spatial phase difference measured across three detectors rejects scattering from non-spherical droplets or multiple droplets in the sampling volume. The signal-processing unit discards readings having a phase shift difference above 6% between the different detectors. This process typically rejects less than 5% of the sampled droplets.

Droplets from the d-DIHEN 10 are probed at both 7 and 15 mm from the nebulizer tip 28 along the centerline of the aerosol. For the Elan 6000 demountable torch, these distances correspond to a position 2 mm (base of the plasma) and 10 mm (induction region) on top of the intermediate tube, respectively. The aerosol is examined in the absence of the quartz torch tubes to prevent scattering of the laser radiation. For each experimental condition, approximately 10,000 droplets are sampled to determine droplet size and velocity distributions. The Sauter mean diameter ($D_{3,2}$), defined as the volume-to-surface area ratio of the aerosol, is used to express the droplet size distribution. Velocities are measured axially along the centerline of the spray and radially with the velocity component perpendicular to the centerline. Values of $D_{3,2}$ and mean velocities represent an average of three measurements (approximately 30,000 droplets). For measurements on a single d-DIHEN 10, the precision (% RSD) ranges from 0.5–1.2% (7 mm) and 0.6–1.6% (15 mm) for $D_{3,2}$ and varies from 0.2–1.1% (7 mm) and 0.2–1.6% (15 mm) for mean velocities. Larger % RSD values are expected (up to 10–15%) if several nebulizers are tested. This increase is due to variations in the aerosol probing position, particularly if the d-DIHEN 10 is disassembled and reassembled.

For analytical measurements, a 10 ng/mL, multielement stock solution is prepared by diluting 1000 μg/mL stock solutions with 2% high-purity HNO$_3$ in 18.3 MΩ·cm distilled deionized water (DDW). For the aerosol diagnostic measurements, only DDW is used. Method validation is accomplished using a reference material Lyphochek Urine Metals Control at both low (Level 1) and high (Level 2) concentrations. The sample is reconstituted in 25.0 mL of DDW and diluted 1:5 with DDW prior to analysis. A 10-ng/mL spike of $^{103}$Rh$^+$ is used as an internal standard, and a five-point standard addition curve is used to quantify elemental concentrations. Between samples, a 2% HNO$_3$ rinse is used to minimize the total dissolved solids burden on the ICPMS interface.

The extent of desolvation, vaporization, excitation and ionization processes and droplet sizes, droplet velocities, span largely control precision of analytical measurements in plasma spectrometry, and the number and volume of droplets introduced to the ICP. Unlike conventional nebulizers-spray chamber arrangements, which introduce the tertiary aerosol into the plasma, direct injection nebulizers generate the aerosol below (approximately 2–5 mm) the base of the ICP. The quality of the primary aerosol is therefore significant because of the absence of a spray chamber or desolvator to remove larger droplets. For plasma spectrometry, the ideal nebulizer generates small monodisperse droplets (span=0) moving with equal velocities. Any deviation from these ideal criteria will degrade sample utilization, detection limits, sensitivity, and precision. Additionally, vaporization and ionization processes in the vicinity of larger droplets are likely to be suppressed, leading to significant fluctuations in signal near desolvating and vaporizing droplets.

In previous experiments with the DIHEN and LB-DIHEN, the solution capillary was flush with the nebulizer gas nozzle. The position of the solution capillary with respect to the nebulizer tip significantly affects the quality of aerosol produced. One benefit of the d-DIHEN 10 is the ability to tune or laterally displace the solution capillary 26 easily with the capillary adjustment adapter 16 during aerosol diagnostic studies or the optimization of the ICPMS signal. At the optimal position, the solution capillary 26 of the d-DIHEN 10 is preferably extended 0.1 mm from the nebulizer tip 28, the condition used for all experiments described below. Any deviation from this position quickly degrades the average droplet size and ICPMS sensitivity by a factor of 2 and 5, respectively.

Previous aerosol diagnostic experiments with the DIHEN and LB-DIHEN also focused on measurements at 15 mm from the nebulizer tip, which corresponds to a position within the load coil region, 13 mm from the end of the intermediate tube. For the d-DIHEN 10, which is positioned 3 mm further back than the DIHEN or LB-DIHEN, this represents a position 10 mm from the end of the intermediate tube in the load coil region. Probing the aerosol at 7 mm provides characteristics that better approximate the quality of spray entering the plasma than measurement at 15 mm from the nebulizer tip.

Droplet size and velocity distributions of the d-DIHEN 10, along with cumulative droplet count and volume percent, for nebulizer gas flow rates ranging from 0.2 to 1.0 L/min probed at 7 and 15 mm from the nebulizer tip 28 are illustrated in FIGS. 2–4. The cumulative data represent all droplets having a diameter of 8 μm or less. In argon ICP, droplets below 8–10 μm in diameter generally contribute favorably to signal intensity because they are the most easily desolvated-vaporized-atomized.

Several interesting observations can be made at both probing positions. First, a multimodal distribution (FIG. 2A) is observed at 15 mm, similar to previous observations for the DIHEN and LB-DIHEN. The multimodal distribution may be attributed to droplet-droplet collisions and formation of a greater number of larger droplets due to coalescence followed by droplet separation. Second, at 0.2 L/min, conditions under which the DIHEN and LB-DIHEN typically operate, the $D_{3,2}$ (and cumulative count percent of droplets 8 μm or less, FIGS. 3A and 3B) of the d-DIHEN 10 aerosol is 7.2 μm (92%) and 7.9 μm (87%) at 7 and 15 mm from the tip of the nebulizer 28, respectively. Clearly, a large number of small droplets are produced under conditions suitable for ICPMS measurements. As the nebulizer gas flow is increased to 1.0 L/min, the $D_{3,2}$ decreases to 5.1 and 6.0 μm at 7 and 15 mm, respectively, while the cumulative count percent of droplets is increased to 98% and 95%, respectively. These $D_{3,2}$ values at 15 mm and a nebulizer gas flow rate of 0.2 L/min are slightly less than the average droplet diameter (9.0 μm) for the DIHEN[39] and nearly half that of the LB-DIHEN (20.1 μm). Relatedly, the cumulative count percent of droplets 8 μm or less is 87%, 80%, and 50% for the d-DIHEN 10, DIHEN, and LB-DIHEN, respectively.

The above data collectively suggest that the droplet diameters (and cumulative count percent) obtained with the d-DIHEN 10 are slightly smaller (larger) than the DIHEN, regardless of nebulizer gas flow rate. Clearly, the critical dimensions for the two nebulizers are nearly identical based on Table 2, but the gas-liquid interaction may be enhanced in the d-DIHEN 10 perhaps because the solution capillary 26 is extended by 0.1 mm beyond the gas orifice, which allows slight oscillations of the capillary. This increased interaction results in formation of a larger volume or mass of smaller droplets, which has been shown to correlate well with the analytical signal. For example, at 0.2 L/min, the cumulative volume (mass) of droplets having a diameter of 8 μm or less comprise 49% (7 mm) and 43% (15 mm) of the total mass (or volume) of solution for the d-DIHEN 10 compared to 35% and 3% for the DIHEN and LB-DIHEN, respectively. Droplet span can also indicate the breadth of the aerosol distribution. Differences in span [defined as $(D_{90}-D_{10})/D_{50}$ where $D_{10}$, $D_{50}$, and $D_{90}$ are the droplet diameters below which 10, 50, and 90% of the cumulated aerosol volume are found; FIG. 3B] are minimal for the d-DIHEN 10 and DIHEN at 0.2 L/min and 15 mm from the nebulizer tip (1.1 vs. 1.0) and slightly smaller than the LB-DIHEN (1.3). Thus, one should expect similar precisions for the d-DIHEN 10 and DIHEN that are better than those obtained with the LB-DIHEN, which agrees with experimental results. In sum, the data in FIGS. 2 and 3 indicate that the d-DIHEN 10 produces a larger volume (mass) of finer aerosol than the DIHEN or LB-DIHEN, which results in better precision and sensitivity for the d-DIHEN 10, as shown later. It should be noted, however, that a small number of larger droplets constitute more than 50% of the aerosol mass (or volume) generated, and that these directly injected droplets are perhaps not effectively utilized or processed by the ICP before analytical measurements, thus resulting in figures of merit that are less than ideal.

As the nebulizer gas flow is increased to 1 L/min, the cumulative volume of fine aerosol is increased to 82% (7 mm) and 70% (15 mm) for the d-DIHEN 10; that is, the quality of the aerosol is improved compared to nebulization at 0.2 L/min, but the analyte residence time in the plasma is reduced. The requirements of low droplet velocities and a narrow droplet velocity distribution are important for maximizing analyte residence time in the plasma, increasing sensitivity, and reducing signal fluctuations.

FIGS. 4A through 4C present axial and radial droplet velocity distributions for the exemplary d-DIHEN 10 at 7 and 15 mm from the nebulizer tip 28. The radial velocity distribution is shown in FIG. 4B for the d-DIHEN 10 at 15 mm. The radial velocity distribution is approximately the same for the d-DIHEN 10 and DIHEN, regardless of nebulizer gas flow rate, and at distances of 7 and 15 mm from the nebulizer tip 28. However, the axial velocity distribution measured at 7 mm is narrower than the values obtained at 15 mm for the d-DIHEN 10. Further, narrower velocity distributions and lower mean axial velocities are obtained at low nebulizer gas flow rates, which correspond to the optimum analytical conditions for the d-DIHEN 10. The average axial velocity measured for the d-DIHEN 10 at 15 mm (13.2 m/s at 0.2 L/min) is slightly less than that of the DIHEN (13.8 m/s at 0.2 L/min). This difference becomes larger as the nebulizer gas flow is increased to 1 L/min; that is, the average droplet velocity increases to 33.0 m/s for the d-DIHEN 10 and 41.7 m/s for the DIHEN. The lower droplet velocities and the narrower droplet velocity distribution of the d-DIHEN 10 aerosol help confine the aerosol to the axial channel, thereby enhancing droplet-plasma interactions and desolvation-atomization-ionization of droplets, thereby leading to higher sensitivity and better precision.

Plots of signal intensity are shown in FIGS. 5A through 5C as a function of Radio Frequency (RF) power, nebulizer gas flow rate, and solution uptake rate for several elements across the mass range using the d-DIHEN 10 and for an optimum intermediate gas flow rate of 1.2 L/min. In all cases, maximum sensitivities are achieved at high RF powers (1.5–1.6 kW) for the d-DIHEN 10, similar to the results obtained with the DIHEN and LB-DIHEN. The optimum nebulizer gas flow rate is 0.16 L/min for a solution uptake rate of 80–100 µL/min. At nebulizer gas flow rates less than 0.10 L/min, the plasma becomes unstable and begins to flicker due to poor nebulization; that is, formation of large droplets.

In general, these conditions are approximately the same as those for the DIHEN, mainly because the dimensions of the d-DIHEN 10 and DIHEN are nearly identical, resulting in similar solution-gas interactions and thus aerosol properties. Two main differences exist between the two nebulizers.

First, the solution capillary 26 of the d-DIHEN 10 is extended by nearly 0.1 mm from the nebulizer tip 28, whereas it is flush with the DIHEN. Secondly, the optimal position of the d-DIHEN 10 tip is 5 mm below the end of the intermediate tube, that is, 3 mm further rearward than the DIHEN and LB-DIHEN. This position was optimized via the capillary adjustment adapter 16 by monitoring the signal intensity. Moving the nebulizer tip backward (from 2 to 5 mm) resulted in a slight improvement in signal intensity. This attribute reduces the chances of damage to the nebulizer tip 28. Further, droplet residence time in the plasma is increased due to a decrease in droplet velocities. Analytical performance quickly degrades at larger distances from the ICP, perhaps because the aerosol does not pass entirely into the axial channel of the plasma.

The above conditions differ from those obtained by other investigators for two homemade DIHENs. These devices were operated at lower RF power (1050–1200 W), slightly higher nebulizer gas flow rates (0.20–0.23 L/min), and lower solution uptake rate (10–60 µL/min) compared to the d-DIHEN 10. Previous experiments have shown, however, that high power and low injector gas flow rates are required to minimize matrix effects, conditions particularly important for direct injection nebulization because 100% of the sample is introduced into the plasma. No aerosol diagnostic data is available on either homemade DIHEN to indicate if a finer aerosol is produced at lower solution uptake rates which could account for the use of less robust conditions. Our own measurements indicate that a slight decrease (approximately 0.5 µm) in $D_{3,2}$ at low solution uptake rates (5–40 µL/min).

Sensitivity, relative detection limits (3σ of the background), and short-term precision (6 min) for the exemplary d-DIHEN 10, DIHEN, and LB-DIHEN are presented in Table 3 for 16 elements across the mass range. Values listed are obtained under optimized conditions for each nebulizer at solution uptake rates of 85, 85 and 110 µL/min for the d-DIHEN 10, DIHEN, and LB-DIHEN, respectively. In general, the d-DIHEN 10 offers sensitivities which are on average 2.4 (ranges from a factor of 1.1 to 8) and 2.7 (ranges from a factor of 1.5 to 6) times larger than the data provided by the DIHEN and LB-DIHEN, respectively. These improvements in sensitivity result in comparable and improved detection limits vs. the DIHEN and LB-DIHEN, respectively. Short-term precision for the d-DIHEN 10 is comparable to or slightly better than the values for DIHEN, while showing significant improvement over the LB-DIHEN. Long-term stability measured over 4 hours was less than 2% for the majority of elements tested. The improvements in analytical figures of merit are attributed to the better aerosol quality of the d-DIHEN 10 compared to the DIHEN and LB-DIHEN. Due to the sequential nature of the quadrupole mass spectrometer, precision may be improved further by increasing the integration time per isotope or by monitoring fewer isotopes.

One of the main advantages of the d-DIHEN 10 over the DIHEN is the improved analytical figures of merit at very low solution uptake rates. Sensitivity and precision are listed in Table 4 at solution uptake rates of 5 to 40 µL/min along with detection limits (Table 5) for the d-DIHEN 10 and DIHEN. Reduction of the solution uptake rate by a factor of 15 (85 µL/min to 5 µL/min) decreases sensitivity by a factor of 9 ($^{82}$Se) to 19 ($^{208}$Pb) for the d-DIHEN 10, less severe compared to the reduction for the DIHEN (factor of up to 56) and LB-DIHEN (factor of up to 270). Similarly, the precision of the d-DIHEN 10 at 5 µL/min ranges from 3.3 to 5.8%, values that are still much better than precision obtained for the DIHEN (4.7 to 9.1%) and LB-DIHEN (13 to 17%). In general, the higher sensitivity and better precision of the d-DIHEN 10 at very low solution uptake rates (<10 µL/min) results in lower detection limits for the d-DIHEN (Table 5). The difference in detection limits between the d-DIHEN and DIHEN are minimal, however, as the solution uptake rate is increased.

Because all direct injection nebulizers introduce 100% of the aerosol into the plasma, polyatomic ions occur to a greater extent compared to conventional nebulization with the nebulizer-spray chamber arrangements, particularly when aerosol desolvation is used to minimize polymeric ion formation.

The elevated oxide level in direct injection ICPMS is attributed to increased solvent load and the introduction of a coarser primary aerosol rather than a finer tertiary aerosol into the ICP. A $CeO^+/Ce^+$ oxide ratio of 48% was measured previously for the DIHEN using ICPMS at a solution uptake rate of 85 µL/min. This ratio was reduced to 20% in a collision cell ICPMS, but after a substantial sacrifice of ion intensities. For oxide ions having lower bond strengths than $CeO^+$, the oxide ratios may be reduced to values comparable to conventional nebulization with collision cell ICPMS.

Alternatively, the oxide ion itself may be used for analytical measurements instead of the atomic ion when the $MO^+/M^+$ ratio approaches 100%. While this approach has been utilized in both normal and cool plasmas using the DIHEN, analytical results have not improved substantially because of poorer sensitivities and precision of the oxide ions.

Relative oxide ion intensities and the $Ba^{2+}/Ba^+$ ratio for the d-DIHEN 10 and DIHEN measured in this work are given in Table 6 as a function of solution uptake rate. In general, oxide ratios for the d-DIHEN 10 and DIHEN are low and similar at solution uptake rates of 10 μL/min or less. Above 10 μL/min, the d-DIHEN 10 provides lower oxide ratios than the DIHEN. For example, the oxide levels for Ce increase from 0.63% to 3.8% (d-DIHEN 10) and 0.50% to 7.6% (DIHEN) as the solution uptake rate is increased from 5 μL/min to 85 μL/min. Similar results are observed for other elements. The $Ba^{2+}/Ba^+$ ratios are also lower for the d-DIHEN at all solution uptake rates compared to the DIHEN.

The above oxide ion formation rates are significantly lower than those previously reported for the DIHEN, mainly because the nebulizer was operated at 0.18 L/min in this study, compared to 0.25 L/min previously. Comparison of the last two columns in Table 6 clearly indicates the influence of nebulizer gas flow rate on relative oxide ion intensity. A higher gas flow rate enhances oxide levels up to three-fold due to the higher droplet axial velocities and reduced residence time in the plasma, which in turn negatively affect desolvation and atomization.[50] The reduced oxide levels for the d-DIHEN 10 are likely due to the same effect; that is, the optimal nebulizer gas flow rate (0.16 L/min) is less than that for the DIHEN (0.18 L/min). Increasing the nebulizer gas flow rate of the d-DIHEN 10 from 0.16 L/min to 0.18 L/min should result in a slightly finer aerosol, but the reduced residence time in the plasma would elevate relative oxide ion intensities, approaching those of the DIHEN under the same conditions. Note, however, that the d-DIHEN 10 tip is positioned at a greater distance from the ICP than the DIHEN, and because of the lower axial velocity of the d-DIHEN droplets, relative oxide ion intensities are reduced compared to the levels noted for the DIHEN.

were determined using a five-point standard addition curve with a 10-ng/mL spike of $^{103}Rh$ used as an internal standard. The samples were diluted 1:5 in DDW prior to analysis. For the low concentration (Level 1) samples, excellent agreement between the measured and reference values exist. For the higher concentration (Level 2) samples, the measured values are slightly higher than the reference values but still within the accepted range for the samples. No nebulizer clogging with the d-DIHEN 10 was realized.

To summarize, a demountable direct injection high efficiency nebulizer 10 (d-DIHEN), with a tunable solution capillary, has been developed to reduce chances of nebulizer tip meltdown and improve aerosol quality and analytical figures of merit for inductively coupled plasma (ICP) spectrometries. At optimum operation, the solution capillary can be extended 0.1 mm beyond the nebulizer gas nozzle and the nebulizer tip is positioned 5 mm below the torch intermediate tube. Under these conditions, the d-DIHEN 10 produces a larger volume (mass) of finer droplets than both the DIHEN and LB-DIHEN, along with lower mean droplet velocities than the DIHEN at low solution uptake rates and low nebulizer gas flow rates.

These conditions collectively enhance plasma robustness and increase analyte residence time in the plasma, thereby improving sensitivity, precision, and detection limits while reducing oxide levels, especially at solution uptake rates ranging from 5 μL/min to 40 μL/min. The utility of the d-DIHEN 10 is shown in the analysis of trace metals in urine. Further improvements may be obtained by reducing the diameter of the solution capillary and glass shell to enhance the performance of the d-DIHEN at very low (nL/min) solution uptake rates.

While the invention has been shown and described with reference to certain embodiments thereof, it should be understood by those skilled in the art that various changes in form and details may be made therein without departing from the spirit and scope of the invention as defined by the appended claims and equivalents thereby.

TABLE 1

Key Dimensions and Parameters for the d-DIHEN in Comparison to the DIHEN, LB-DIHEN, HEN, and Conventional TR-30 nebulizers.

|  | d-DIHEN | DIHEN (DIHEN-170-AA) | LB-DIHEN (DIHEN-30-AA) | HEN (HEN-170-AA) | Conventional nebulizer (TR-30-AA) |
|---|---|---|---|---|---|
| Solution capillary i.d. (μm) | 100 | 104 | 318 | 70–110 | 220–320 |
| Capillary wall thickness (μm) | 21 | 20 | 16 | 15–40 | 15–40 |
| Solution capillary o.d. (μm) | 142 | 144 | 350 | 100–190 | 250–400 |
| Gas orifice i.d. (μm) | 175 | 173 | 412 | 150–200 | 350–450 |
| Capillary annulus area (mm$^2$) | 0.00785 | 0.0085 | 0.0794 | 0.0038–0.0095 | 0.05–0.10 |
| Gas annulus area (mm$^2$) | 0.00822 | 0.0094 | 0.0371 | 0.007–0.01 | 0.03–0.04 |

The introduction of samples with high total dissolved solids content, such as urine, can be problematic in ICPMS, especially when direct injection nebulizers are used due to potentially severe matrix and plasma loading effects. Additionally, nebulizer clogging may also occur due to the reduced solution capillary dimensions of microflow nebulizers. Therefore, the analysis of the reference material Lyphochek Urine Metals Control provides a good test of the usability of the d-DIHEN 10. Nine elements (Al, Mn, Co, As, Se, Cd, Hg, Tl and Pb) were tested at both low (Level 1) and high (Level 2) concentration levels. The results of the analysis are given in Table 7. The measured concentrations

TABLE 2

Instrumental Operating Conditions for the Ar ICPMS.

| ICPMS System | PE-Sciex Elan 6000 |
|---|---|
| RE power, W | 1500, 1000–1600 |
| Nominal frequency, MHz | 40 |
| RE generator type | Free-running |
| Induction coil circuitry | 3-turn coil, PLASMALOK™ |
| Sampling depth (above load coil), mm | 11 |

TABLE 2-continued

Instrumental Operating Conditions for the Ar ICPMS.

| | |
|---|---|
| Sampler (orifice diameter, mm) | Nickel, 1.1 |
| Skimmer (orifice diameter, mm) | Nickel, 0.9 |
| Outer gas flow rate, L/min | 15 |
| Intermediate gas flow rate, L/min | 1.2, 0.8–1.6 |

| Sample introduction system | d-DIHEN | DIHEN |
|---|---|---|
| Solution flow rate, μL/min | 5–100 | 5–100 |
| Nebulizer gas flow rate, L/min | 0.16, 0.1–1.0 | 0.18 |
| | 1.0 | |
| Capillary position below intermediate tube, mm | 5 | 2 |
| Total capillary length, cm | 36 | — |
| Support capillary length, cm | 26 | — |
| Capillary length (unsupported), cm | 7 | — |

Data acquisition parameters

| | |
|---|---|
| Scan mode | Peak hopping |
| Points/mass | 1 |
| Resolution, amu | 0.7 |
| Sweeps/Reading | 10 |
| Readings/Replicate | 5 |
| Replicates | 11 |
| Dwell time/mass, ms | 20 |
| Integration time, ms | 1000 |

TABLE 3

Typical Sensitivity, Relative Detection Limits, and Precision in ICPMS Obtained with the d-DIHEN, DIHEN, and LB-DIHEN Nebulizers.[a]

| | Sensitivity (MHz/ppm) | | | Detection Limit (ng/L) | | | Precision (% RSD)[b] | | |
|---|---|---|---|---|---|---|---|---|---|
| Isotope | d-DIHEN | DIHEN | LB-DIHEN | d-DIHEN | DIHEN | LB-DIHEN | d-DIHEN | DIHEN | LB-DIHEN |
| $^{7}$Li | 9.3 | 8 | 6 | 2 | 2 | 4 | 1.4 | 0.6 | 1.5 |
| $^{24}$Mg | 26 | 20 | 13 | 47 | 7 | 10 | 1.5 | 0.6 | 1.5 |
| $^{51}$V | 88 | 30 | 38 | 6 | 2 | 5 | 0.6 | 0.8 | 1.0 |
| $^{55}$Mn | 113 | 65 | 47 | 10 | 2 | 3 | 0.7 | 0.7 | 1.1 |
| $^{59}$Co | 110 | 56 | 36 | 2 | 0.9 | 2 | 0.9 | 0.8 | 1.0 |
| $^{60}$Ni | 25 | 9.9 | — | 8 | 12 | — | 0.6 | 0.7 | — |
| $^{63}$Cu | 41 | 25 | — | 33 | 10 | — | 1.0 | 0.6 | — |
| $^{75}$As | 36 | 4.5 | 6 | 1 | 17 | 26 | 0.9 | 1.3 | 1.9 |
| $^{82}$Se | 3.4 | 0.6 | 0.6 | 12 | 47 | 54 | 1.3 | 1.4 | 1.8 |
| $^{88}$Sr | 161 | 95 | 70 | 1 | 0.9 | 1 | 0.6 | 0.8 | 1.4 |
| $^{103}$Rh | 167 | 91 | 91 | 0.3 | 0.6 | 0.5 | 0.5 | 0.9 | 1.4 |
| $^{115}$In | 193 | 113 | — | 0.5 | 0.6 | — | 0.6 | 0.6 | 1.2 |
| $^{133}$Cs | 201 | 130 | 122 | 0.4 | 0.6 | 0.6 | 0.6 | 0.9 | — |
| $^{208}$Pb | 115 | 76 | 54 | 3 | 2 | 2 | 0.4 | 0.5 | 1.4 |
| $^{232}$Th | 167 | 66 | — | 0.5 | 0.6 | — | 0.5 | 1.2 | — |
| $^{238}$U | 175 | 99 | 91 | 0.4 | 0.3 | 1.2 | 0.4 | 0.8 | 1.1 |

[a]The nebulizer gas flow rate is 0.16 L/min for the d-DIHEN and 0.25 L/min for the DIHEN and LB-DIHEN. The solution uptake rate is 85, 85, and 110 μL/min for the d-DIHEN, DIHEN, and LB-DIHEN, respectively. The d-DIHEN is positioned 5 mm below the torch intermediate tube with the solution capillary extended 0.1 mm beyond the nebulizer gas nozzle.
[b]Measured over 6 minutes using a 10 μg/L multielement solution, N = 11.

TABLE 4

Relative Sensitivities (MHz/ppm) and Precision (% RSD) Obtained for the d-DIHEN, DIHEN, and LB-DIHEN at Low Solution Uptake Rates[a] and 1500 W.

| | Solution Uptake Rate | | | | | | | | |
|---|---|---|---|---|---|---|---|---|---|
| | 5 μL/min | | | 10 μL/min | | | 40 μL/min | | |
| Isotope | d-DIHEN | DIHEN | LB-DIHEN | d-DIHEN | DIHEN | LB-DIHEN | d-DIHEN | DIHEN | LB-DIHEN |
| $^{7}$Li | 0.9 (5.8) | 0.2 (8.1) | 0.3 (15) | 1.8 (3.7) | 0.3 (6.5) | 0.6 (11) | 7.4 (2.2) | 3 (2.5) | 2 (2.4) |
| $^{51}$V | 5.3 (4.8) | 2 (4.7) | 1 (15) | 11 (2.2) | 4 (3.9) | 3 (13) | 48 (2.2) | 20 (1.7) | 11 (3.1) |
| $^{55}$Mn | 6.9 (3.6) | 2 (5.8) | 2 (17) | 15 (2.5) | 4 (5.3) | 4 (13) | 63 (2.2) | 25 (1.2) | 14 (3.6) |
| $^{59}$Co | 6.1 (4.3) | 1 (6.7) | 1 (16) | 13 (2.3) | 3 (5.4) | 3 (14) | 56 (1.9) | 18 (1.2) | 11 (2.9) |
| $^{60}$Ni | 1.3 (5.2) | — | — | 2.7 (2.6) | — | — | 11 (2.2) | — | — |
| $^{63}$Cu | 4.1 (6.2) | — | — | 8.6 (2.2) | — | — | 35 (1.8) | — | — |
| $^{75}$As | 3.4 (4.1) | 0.3 (6.2) | 0.3 (15) | 7.0 (3.0) | 0.6 (4.7) | 0.5 (14) | 25 (1.7) | 4 (1.3) | 2 (3.2) |
| $^{82}$Se | 0.4 (3.8) | 0.1 (6.9) | 0.1 (13) | 0.7 (3.0) | 0.1 (5.9) | 0.1 (9.1) | 2.5 (1.8) | 0.4 (3.1) | 0.2 (3.8) |

TABLE 4-continued

Relative Sensitivities (MHz/ppm) and Precision (% RSD) Obtained for the d-DIHEN, DIHEN, and LB-DIHEN at Low Solution Uptake Rates[a] and 1500 W.

| | Solution Uptake Rate | | | | | | | | |
|---|---|---|---|---|---|---|---|---|---|
| | 5 μL/min | | | 10 μL/min | | | 40 μL/min | | |
| Isotope | d-DIHEN | DIHEN | LB-DIHEN | d-DIHEN | DIHEN | LB-DIHEN | d-DIHEN | DIHEN | LB-DIHEN |
| $^{88}$Sr | 11 (4.9) | 4 (7.3) | 4 (15) | 21 (2.7) | 10 (5.6) | 8 (13) | 82 (2.3) | 68 (1.8) | 29 (3.3) |
| $^{103}$Rh | 11 (3.8) | 3 (7.1) | 3 (17) | 22 (2.5) | 8 (5.2) | 6 (13) | 93 (1.6) | 50 (1.6) | 23 (2.6) |
| $^{115}$In | 12 (4.7) | — — | — — | 26 (2.6) | — — | — — | 106 (1.8) | — — | — — |
| $^{133}$Cs | 13 (3.3) | 6 (9.1) | 5 (15) | 18 (2.2) | 15 (4.9) | 11 (13) | 113 (1.8) | 86 (1.4) | 38 (2.5) |
| $^{208}$Pb | 6 (4.2) | 3 (7.6) | 2 (15) | 12 (1.8) | 7 (5.7) | 5 (12) | 51 (1.6) | 37 (0.9) | 16 (2.6) |
| $^{232}$Th | 11 (4.7) | — — | — — | 22 (2.0) | — — | — — | 91 (1.7) | — — | — — |
| $^{238}$U | 11 (3.6) | 6 (6.8) | 5 (14) | 22 (2.1) | 11 (5.0) | 11 (12) | 93 (1.6) | 80 (0.9) | 33 (2.0) |

[a]The nebulizer gas flow rate is 0.16, 0.17, and 0.25 L/min for the d-DIHEN, DIHEN, and LB-DIHEN, respectively. Actual solution uptake values for the DIHEN and LB-DIHEN are 5.6, 11, and 42 μL/min. The d-DIHEN is positioned 5 mm below the torch intermediate tube with the solution capillary extended 0.1 mm beyond the nebulizer gas nozzle.

TABLE 5

Relative Detection Limits for the d-DIHEN and DIHEN at Low Solution Uptake Rates[a] and 1500 W.

| | Solution Uptake Rate | | | | | |
|---|---|---|---|---|---|---|
| | 5 μL min$^{-1}$ | | 10 μL min$^{-1}$ | | 40 μL min$^{-1}$ | |
| Isotope | d-DIHEN-175 | DIHEN | d-DIHEN-175 | DIHEN | d-DIHEN-175 | DIHEN |
| $^{7}$Li | 2 | 1500 | 22 | 380 | 5 | 62 |
| $^{51}$V | 18 | 230 | 23 | 67 | 25 | 10 |
| $^{55}$Mn | 19 | 870 | 15 | 260 | 15 | 25 |
| $^{59}$Co | 13 | 340 | 5.6 | 78 | 3 | 11 |
| $^{60}$Ni | 36 | 750 | 37 | 320 | 20 | 35 |
| $^{75}$As | 15 | 650 | 10 | 180 | 3 | 52 |
| $^{82}$Se | 202 | 12000 | 72 | 4500 | 24 | 570 |
| $^{103}$Rh | 7 | 38 | 3 | 30 | 2 | 3 |
| $^{115}$In | 5 | 44 | 3 | 17 | 2 | 2 |
| $^{133}$Cs | 5 | 45 | 2 | 13 | 1 | 4 |
| $^{208}$Pb | 18 | 45 | 15 | 25 | 16 | 4 |
| $^{232}$Th | 7 | 26 | 4 | 5 | 1 | 2 |
| $^{238}$U | 4 | 20 | 2 | 7 | 1 | 2 |

[a]Actual solution uptake rates for the DIHEN are 5.6, 11, and 42 μL/min. The nebulizer gas flow rate is 0.16 L/min for the d-DIHEN and 0.17 L/min for the DIHEN. The d-DIHEN is positioned 5 mm below the torch intermediate tube with the solution capillary extended 0.1 mm beyond the nebulizer gas nozzle.

TABLE 6

Oxide and Doubly Charged (%) Ratios with the d-DIHEN and DIHEN Measured at Different Solution Uptake Rates and 1500 W.[a]

| | Solution Uptake Rate | | | | | | | | |
|---|---|---|---|---|---|---|---|---|---|
| | 5 μL/min | | 10 μL/min | | 40 μL/min | | 85 μL/min | | |
| | d-DIHEN | DIHEN | d-DIHEN | DIHEN | d-DIHEN | DIHEN | d-DIHEN | DIHEN | DIHEN[b] |
| BaO$^+$:Ba$^+$ | 0.02% | 0.02% | 0.02% | 0.02% | 0.06% | 0.11% | 0.15% | 0.29% | 0.55% |
| CeO$^+$:Ce$^+$ | 0.63% | 0.50% | 0.79% | 0.78% | 2.0% | 2.8% | 3.8% | 7.6% | 27% |
| YO$^+$:Y$^+$ | 0.21% | 0.22% | 0.18% | 0.29% | 0.62% | 0.98% | 1.3% | 2.4% | 6.6% |
| TbO$^+$:Tb$^+$ | 0.24% | 0.21% | 0.31% | 0.33% | 0.85% | 1.3% | 1.8% | 3.2% | 8.1% |
| HoO$^+$:Ho$^+$ | 0.11% | 0.12% | 0.12% | 0.17% | 0.33% | 0.61% | 0.78% | 1.4% | 2.2% |
| ThO$^+$:Th$^+$ | 1.3% | 0.88% | 1.5% | 1.4% | 3.5% | 4.7% | 6.4% | 14% | 43% |
| UO$^+$:U$^+$ | 1.1% | 0.83% | 1.5% | 1.3% | 3.6% | 4.0% | 6.2% | 9.4% | 23% |
| Ba$^{2+}$:Ba$^+$ | 0.67% | 1.2% | 0.76% | 1.4% | 1.0% | 2.1% | 1.5% | 1.9% | 1.1% |

[a]The nebulizer gas flow rate is 0.16 and 0.18 L/min for the d-DIHEN and DIHEN, respectively, unless otherwise indicated. The d-DIHEN is positioned 5 mm below the torch intermediate tube with the solution capillary extended 0.1 mm beyond the nebulizer gas nozzle.
[b]Nebulizer gas flow rate = 0.25 L/min

TABLE 7

Analysis of Reference Material - Trace Metals in Urine at Low (Level 1) and High (Level 2) Concentrations.[a]

| | Level 1 | | | Level 2 | | |
|---|---|---|---|---|---|---|
| Isotope | measured Concentration (ng/mL ± 1σ)[b] | Reference Concentration (ng/mL) | Range (ng/mL) | Measured Concentration (ng/mL ± 1σ) | Reference Concentration (ng/mL) | Range (ng/mL) |
| $^{27}$Al | 25.9 ± 0.3 | 28 | (23–34) | 52 ± 5 | 51 | (41–62) |
| $^{55}$Mn | 1.4 ± 0.1 | 1.6 | (1.3–1.9) | 24.2 ± 0.2 | 20.3 | (16.2–24.3) |
| $^{59}$Co | 3.7 ± 0.1 | 3.6 | (2.8–4.3) | 11.8 ± 0.1 | 10.6 | (8.5–12.7) |
| $^{75}$As | 54 ± 1 | 59 | (47–71) | 174 ± 1 | 151 | (121–182) |
| $^{82}$Se | 82 ± 1 | 81 | (65–97) | 285 ± 3 | 249 | (199–299) |
| $^{114}$Cd | 6.3 ± 0.1 | 5.9 | (4.7–7.1) | 12.5 ± 0.1 | 10.9 | (8.7–13.1) |
| $^{202}$Hg | 39.5 ± 0.5 | 40 | (32–47) | 110 ± 1 | 99 | (79–119) |
| $^{205}$Tl | 10.0 ± 0.3 | 9.8 | (7.8–11.7) | 220 ± 5 | 188 | (150–226) |
| $^{208}$Pb | 13.5 ± 0.3 | 13.9 | (11.1–16.6) | 80 ± 1 | 74 | (59–88) |

[a]The nebulizer gas flow rate, solution flow rate, and RF power are 0.16 L/min, 80 μL/min, and 1500 W, respectively. The d-DIHEN is positioned 5 mm below the torch intermediate tube with the solution capillary extended 0.1 mm beyond the nebulizer gas nozzle.
[b]Measured concentrations were determined using a five-point standard addition curve with a 10-ng/mL spike of $^{103}$Rh as an internal standard.

What is claimed is:

1. A nebulizer adapted for adjusting a position of a capillary tube contained within said nebulizer, comprising:
   an elongated tubular shell having a gas input port and a gas output port;
   a capillary adjustment adapter for displacing the capillary tube in a lateral direction via a rotational force; and
   a connector for connecting the elongated tubular shell, the capillary adjustment adapter and the capillary tube;
   wherein said elongated tubular shell is configured for direct injection into a flame or a plasma without pre-filtering, and
   said displacing of the capillary tube facilitates optimization of said direct injection.

2. The nebulizer of claim 1, wherein the capillary adjustment adapter comprises:
   a first rotational member for holding the capillary tube via an O-ring and for displacing the capillary tube; and
   a second rotational member for supporting the capillary tube and exerting pressure against the O-ring such that the first rotational member increases the pressure holding the capillary tube.

3. The nebulizer of claim 1, further comprising:
   a supporting tube enclosing the capillary tube and providing support for the capillary tube.

4. The nebulizer of claim 1, wherein the rotational force comprises at least one of a manual force and a motorized force.

5. The nebulizer of claim 1, wherein said capillary tube includes a sample input port and a sample output port.

6. The nebulizer of claim 5, wherein said gas output port of said elongated tubular shell comprises a nozzle.

7. The nebulizer of claim 6, wherein the controller is adapted to determine a distance between the nozzle of said elongated tubular shell and the sample output port of said capillary tube via a rotational displacement of said capillary adjustment adapter.

8. The nebulizer of claim 1, further comprising:
   a controller for controlling a motor for displacing the capillary tube via the capillary adjustment adapter.

9. The nebulizer of claim 1, wherein the connector comprises a T shaped connector a having a sample input port, a gas input port and a gas output port.

10. The nebulizer of claim 9, wherein the connector comprises Teflon.

11. A modular nebulizer comprising:
    an elongated tube having an open first end and a tapered second end leading to a nozzle;
    a connector for connecting the elongated tube to a sample and to a gas;
    a solution capillary for conveying a sample to the nozzle of the elongated tube; and
    a capillary adjustment adapter for displacing the solution capillary in a lateral direction;
    wherein said elongated tubular shell is configured for direct injection into a flame or a plasma without pre-filtering, and
    said displacing of the capillary tube facilitates optimization of said direct injection.

12. The modular nebulizer of claim 11, wherein the elongated tube comprises borosilicate.

13. The modular nebulizer of claim 11, wherein the connector comprises a T shaped connector.

14. The modular nebulizer of claim 13, wherein the connector comprises one of a high temperature resistant plastic material, a glass material and a metallic material.

15. The modular nebulizer of claim 13, wherein the T shaped connector comprises a sample port, a gas input port and an output port.

16. The modular nebulizer of claim 15, wherein the elongated tube is connected to the T shaped connector via the output port.

17. The modular nebulizer of claim 11, wherein the high temperature resistant plastic material comprises Teflon.

18. The modular nebulizer of claim 11, wherein the capillary adjustment adapter displaces the solution capillary in the lateral direction via a rotational force.

19. The modular nebulizer of claim 18, wherein the capillary adjustment adapter is connected to the sample port of the T shaped connector.

* * * * *